(12) United States Patent
Vogt et al.

(10) Patent No.: US 8,696,762 B2
(45) Date of Patent: Apr. 15, 2014

(54) IMPLANT OF CROSS-LINKED SPIDER SILK THREADS

(75) Inventors: Peter Vogt, Hannover (DE); Christina Allmeling, Peine (DE); Kerstin Reimers, Hannover (DE)

(73) Assignee: Medizinische Hochschule Hannover, Hannover (DE)

( * ) Notice: Subject to any disclaimer, the term of this patent is extended or adjusted under 35 U.S.C. 154(b) by 975 days.

(21) Appl. No.: 12/518,638

(22) PCT Filed: Dec. 11, 2006

(86) PCT No.: PCT/EP2006/069562
§ 371 (c)(1), (2), (4) Date: May 11, 2010

(87) PCT Pub. No.: WO2008/071226
PCT Pub. Date: Jun. 19, 2008

(65) Prior Publication Data
US 2010/0228359 A1   Sep. 9, 2010

(51) Int. Cl.
*A61F 2/02* (2006.01)
(52) U.S. Cl.
USPC ........................................................ 623/23.72
(58) Field of Classification Search
USPC ........................................................ 623/23.72
See application file for complete search history.

(56) References Cited

U.S. PATENT DOCUMENTS

| | | | |
|---|---|---|---|
| 5,019,087 A | 5/1991 | Nichols | |
| 5,656,605 A | 8/1997 | Hansson et al. | |
| 5,756,457 A | 5/1998 | Wang et al. | |
| 5,925,053 A | 7/1999 | Hadlock et al. | |
| 6,103,255 A * | 8/2000 | Levene et al. | 424/426 |
| 6,436,129 B1 | 8/2002 | Sharkey et al. | |
| 6,626,950 B2 * | 9/2003 | Brown et al. | 623/23.72 |
| 6,716,225 B2 | 4/2004 | Li et al. | |

(Continued)

FOREIGN PATENT DOCUMENTS

| | | |
|---|---|---|
| EP | 1 084 686 | 3/2001 |
| WO | WO 2005/094911 | 10/2005 |
| WO | WO 2006/008163 | 1/2006 |
| WO | WO 2006/030182 | 3/2006 |

OTHER PUBLICATIONS

Gregory H. Altman et al., "Silk-Based Biomaterials", *Biomaterials*, vol. 24, 2003, pp. 401-416.

(Continued)

*Primary Examiner* — Gregory Anderson
(74) *Attorney, Agent, or Firm* — Greer, Burns & Crain Ltd.

(57) ABSTRACT

The present invention provides the use of spider silk threads for the production of tissue implants for medical use. A scaffolding matrix is provided for implantation, which matrix is comprised of spider silk thread and/or segments of spider silk threads which are cross-linked. The cross-linked spider silk thread segments essentially maintain a three-dimensional shape into which it is formed by pressing between molds. The three-dimensional shape obtainable by molding sufficiently stable to be used as an implant or for colonizing by mammalian cells while essentially maintaining the three-dimensional shape. In a further embodiment, the scaffolding matrix of cross-linked spider silk segments is at least partially covered by cells autologous or heterologous to the implant recipient. The matrix colonized with cells is obtainable by in vitro cultivation of isolated cells in suspension with the scaffolding matrix.

14 Claims, 1 Drawing Sheet

(56) References Cited

U.S. PATENT DOCUMENTS

| | | |
|---|---|---|
| 7,041,797 B2 * | 5/2006 | Vollrath ..................... 530/353 |
| 7,198,799 B2 | 4/2007 | Mueller et al. |
| 7,775,965 B2 | 8/2010 | McFetridge |
| 8,106,014 B2 | 1/2012 | Priestley et al. |
| 2002/0168338 A1 | 11/2002 | Baird |
| 2003/0100108 A1 | 5/2003 | Altman et al. |
| 2004/0102793 A1 | 5/2004 | Yaszemski et al. |
| 2005/0013844 A1 | 1/2005 | Hadlock et al. |
| 2005/0260706 A1 | 11/2005 | Kaplan et al. |
| 2006/0282173 A1 | 12/2006 | McFetridge |
| 2007/0087024 A1 | 4/2007 | Knight |
| 2007/0113355 A1 | 5/2007 | Knight |
| 2008/0249639 A1 | 10/2008 | Gu et al. |
| 2008/0274155 A1 | 11/2008 | Barton et al. |
| 2010/0056438 A1 * | 3/2010 | Scheibel et al. ................ 514/12 |
| 2010/0222863 A1 | 9/2010 | Gravett et al. |
| 2010/0256756 A1 | 10/2010 | Altman et al. |
| 2012/0023677 A9 | 2/2012 | Knight |

OTHER PUBLICATIONS

A.C. MacIntosh et al., "Evaluation of Spider Silks for Cartilage Tissue Engineering Applications", presented at 7$^{th}$ *World Biomaterials Congress*, May 17-21, 2004, pp. 1531.

F. Vollrath et al., "Local Tolerance to Spider Silks and Protein Polymers In Vivo", in vivo, vol. 16, 2002, pp. 229-234.

Allmeling, Christina, et. al., "Use of spider silk fibres as an innovative material in a biocompatible artificial nerve conduit", *J. Cell. Mol. Med.*, vol. 10, No. 3, 2006 pp. 770-777.

* cited by examiner

IMPLANT OF CROSS-LINKED SPIDER SILK THREADS

The present invention relates to implants suitable for the reconstruction of tissue defects, preferably to soft tissue implants. In detail, the present invention relates to a novel scaffolding matrix having a pre-determined three-dimensional shape for use as an implant and, in a further embodiment, to an implant comprising the scaffolding matrix and having adherent heterologous, preferably autologous cells or tissue.

For the generation of soft tissue implants comprising a scaffolding matrix of the invention with adherent tissue, the matrix is provided with heterologous or autologous tissue by in vitro cultivation of the scaffolding matrix with the desired heterologous or autologous cells. During the in vitro cultivation of the scaffolding matrix with mammalian cells, the cells adhere to and colonize the scaffolding matrix, essentially maintaining the three-dimensional shape of the matrix.

STATE OF THE ART

US 2003/0100108 A1 discloses the formation of an artificial ligament comprised of silk worm fibres onto which bone marrow stroma cells are grown in vitro to induce de novo ligament tissue formation prior to implantation. The disclosure emphasizes the mechanical strength of silk fibres obtained from *Bombyx mori*, which silk worm fibres are used throughout the examples. Without demonstrating the suitability of fibres from spiders, *Nephila clavipes* is mentioned as an alternative source for silk along with silks obtainable from genetically engineered bacteria or eucaryotic cells, silks obtained from cultured cells of silk worms or spiders, native silks, cloned full or partial sequences of native silks, as well as silks obtained from genetic genes encoding silk or silk-like sequences.

WO 2005/094911 A2 discloses a composite material for the formation of surgically implantable devices, including sutures, artificial ligaments and tendons, which composite material consists of a matrix material containing silk elements. As the matrix material, a cross-linked fibroin or cross-linked casein matrix or an acrylic matrix made of cyano acrylate is preferred, which matrix materials are preferably cross-linked and known to be biocompatible.

DE 10053611 A1 describes a tube implant that is said to be suitable for fostering the growth of nerve cells, which tubes have mono-filaments arranged axially in their inner volume. The mono-filaments as well as the tube consist of synthetic polymers.

WO 01/56626 A1 describes a solid film, adhesive or sealant and a suture for medical use composed of spider silk monomers, either by itself or in combination with a bio compatible polymer, e.g. hyaluronic acid, polyester, collagen or elastin. The disclosure concentrates on producing silk by heterologous expression of the silk encoding sequences for mass production. Starting from the monomers that are produced by biotechnological methods, synthetic fibres are made by extrusion using wet spinning, dry spinning, melt spinning or dry-jet spinning. The synthetic mono-filaments can further be twisted and entangled to form yarns, which may further be weaved, knitted or braided into fabrics.

Vollrath et al. (In Vivo 229-234 (2002)) investigated the suitability of spider silk threads for medical applications by implanting a bundle of silk obtained from *Nephila clavipes* spiders into a subcutaneous wound of a pig.

Allmeling et al. (J. of Cellular and Molecular Medicine, Vol. 10, No. 3, 2006) describe the use of non-modified spider dragline silk threads for guiding the growth of nerve cells across a defective site of nerve tissue.

From the state of art, no matrix is known that can be moulded into a pre-determined three-dimensional form while allowing an effective reconstruction of tissue defects, e.g. by using the matrix for the production of a medical product for the treatment of tissue defects, the matrix either without or with being colonized by mammalian cells.

Further, no implantable material is known that can be used for the production of a medical product for the treatment of wetting, seroserous and/or serosangiuneous wounds for promoting healing, especially infectious wounds.

OBJECTS OF THE INVENTION

In view of the known state of art, it is an object of the present invention to improve the deficiencies of the state of art and to provide a scaffolding matrix that can be used for the production of a medical product having a pre-determined three-dimensional shape, e.g. an implant or a soft tissue implant for filling tissue defects or replacing defective tissue in mammals. It is a special object to provide a soft tissue implant comprising specified mammalian cells or tissue while having a pre-determined three-dimensional shape.

A further object is the provision of a composition for medical use, which composition serves to heal seroserous and/or serosanguineous wound surfaces.

GENERAL DESCRIPTION OF THE INVENTION

The present invention attains the above-mentioned objects by providing tissue made of spider silk threads and, preferably, three-dimensionally moulded shapes comprising cross-linked spider silk threads, wherein the threads essentially have the structure and surface as obtainable from spiders, preferably from *Nephila clavipes*.

In a first embodiment, the present invention provides the use of spider silk threads for the production of tissue implants for medical use. In this embodiment, the scaffolding matrix is provided for implantation, which matrix is comprised of spider silk thread and/or segments of spider silk threads which are cross-linked. The cross-linked spider silk thread segments essentially maintain a three-dimensional shape into which it is formed, e.g. by pressing between moulds. The three-dimensional shape obtainable by moulding is sufficiently stable to be used as an implant or for colonization by mammalian cells while essentially maintaining the three-dimensional shape. Accordingly, in a specific further embodiment, the scaffolding matrix of cross-linked spider silk segments is at least partially covered by cells autologous or heterologous to the implant recipient. The matrix colonized with cells is obtainable by in vitro cultivation of isolated cells in suspension with the scaffolding matrix.

Preferably, the three-dimensional matrix is colonized with cells of the cell type which is predominantly and naturally occurring in the body part or tissue to be replaced by the implant. Colonization of the matrix by cells can be obtained by incubating the matrix with a suspension of the desired cell type under otherwise conventional cell culture conditions. Cultivation can be performed until the matrix is provided with some cells adhering, to confluency of cells, or to a state where cells form aggregates. Preferably, the implant is integrated into a recipient in a state before cell aggregate formation occurs in order to allow the natural organization of tissue growth, including the colonization with different cell types to occur in the site of implantation under natural conditions, e.g. the ingrowth of vessels.

The cross-linking of spider silk segments is only required for imparting a certain structural stability to a three-dimensional scaffolding matrix, which three-dimensional form can e.g. be generated by moulding. Accordingly, cross-linking is preferably obtained by cross-linking agents that do not alter the cell adhesive properties of the spider silk threads. Therefore, the addition of a further bulk matrix compound to produce a composite matrix is unnecessary according to the invention.

In a second embodiment, the present invention relates to the use of spider silk threads for the production of a wound dressing for medical use, wherein the wound is a superficial or internal lesion with impaired, retarded or essentially absent healing properties, e.g. having impaired or blocked regeneration of tissue. The impaired or blocked regeneration of tissue may for example result in an impairment or lack of closure of the wound, e.g. impaired fusion and healing of adjacent surfaces of the wound, or impairment or block of generation of superficial tissue, e.g. of epithelial tissue, e.g. skin.

The preferred wounds for treatment with the wound dressing according to this embodiment of the invention are seroserous and/or serosanguineous wounds. In this embodiment, the properties of spider silk threads for promoting the growth of mammalian cells and inhibiting the occurrence of infections are exploited. One example for this embodiment is the use of spider dragline silk obtained from *Nephila clavipes* for the production of a superficial wound dressing, essentially consisting of silk threads arranged in a sheet-like manner, for covering of seroserous or serosanguineous wounds, e.g. diabetic ulcer or venous ulcer.

In both embodiments, the advantageous properties of spider silk threads for medical use are exploited, namely its properties to enhance cell growth even under adverse conditions like e.g. in a seroserous wound or under the conditions of in vitro cultivation, while no chemical derivatisation or treatment of the spider silk obtainable from producer spiders, preferably *Nephila clavipes*, are required, except for the cross-linking in the case of the scaffolding matrix. After implantation of the implants according to the invention into a mammal, it can be observed that the site of the implantation and the surrounding tissue is not impaired or affected negatively by the presence of the scaffolding matrix. Accordingly, it is an advantage of the implants of the present invention that no synthetic or natural components are comprised in concentrations which lead to the destruction or impairment of tissue at the site of the implantation. Following a longer period of time after implantation, the scaffolding matrix of the implant cannot be detected, i.e. is degraded, again without leaving a negative impact onto tissue at the site of the implantation. Consequently, the scaffolding matrix of the invention provides for a structurally stable implant for the replacement of a tissue defect, which scaffolding matrix supports growth of the tissue at the site of implantation and which is degraded by the recipient, leaving the immunologically tolerated tissue, e.g. autologous tissue, at the site of implantation only. This is a specific advantage over implants essentially consisting of synthetic copolymers, often resulting in an acidification of the site of implantation by degradation products.

In detail, the spider silk threads, whether cross-linked to a three-dimensional scaffolding matrix, or used as a non-woven tissue, after some time following implantation were completely absorbed by the recipient of the implant. As a result, no foreign substances are present at the site of the implant after a period of 2 to twelve months. This demonstrates one of the major advantages of the implants according to the invention, namely the provision of a functional implant for replacement of the tissue defect by the functional implant without occurrence of an adverse immunological reaction and without accumulation of deposits of the implant. In addition, no foreign substances, namely none of the spider silk threads, as well as no cross-linking agent, can be found following some time after the implantation, leaving the reconstituted tissue in the place of the implant that replaced the original tissue defect.

DETAILED DESCRIPTION OF THE INVENTION

In general, the present invention utilizes spider silk, preferably the major ampullate or dragline thread of spiders, preferably of *Nephila clavipes*. The dragline silk can be obtained from spiders, preferably from the female spiders by sedating them with carbon dioxide or by cooling them to a temperature of about 4° C., fixing them to a surface and winding the thread. The speed for pulling and winding the thread can correspond to the falling speed of the spider as the major ampullate is the life line of the spider.

The spider silk thread obtained freshly is essentially sterile and can be used directly for cell culture or for the production of the products for medical use according to the invention without further sterilization, provided sterile equipment and a sterile atmosphere are used.

According to the first embodiment, a scaffolding matrix having a three-dimensional form is generated from the spider silk by moulding a mixture comprising spider silk thread segments and a cross-linking agent into a desired shape. The silk segments can be produced by cutting, e.g. using a homogenizer to obtain smaller segments of the spider silk. The segments can have the size of 20 cm down to 0.1 mm, preferably in a range of 10 cm to 1 mm, more preferably 10 to 1 mm. For moulding, the spider silk segments and the cross-linking agent can be used in an aqueous mixture and/or in a solvent, or in a dry mixture.

Depending on the cross-linking agent, the addition of a catalyst to promote the formation of bonds between the cross-linking agent and the silk threads can be advantageous, or moulding at elevated temperatures.

For cross-linking, cross-linking agents are preferred that form a chemical link between at least two superficial areas of silk segments, e.g. a link between at least two segments, without essentially altering the surface characteristics of the spider silk. Examples of cross-linking agents are bi- and trifunctional organic compounds having carboxylic acid residues, e.g. selected from the group comprising ABH (p-azidobenzoyl hydrazide), AMAS (N-α-maleimidoacetoxy)-succinimide ester), ANB-NOS (N-5-azido-2-nitrobenzyloxysuccinimide), APDP (N-(4-[p-azidosalicylamido]butyl)-3'-(2'-pyridyldithio) propionamide), APG (p-azidophenyl glyoxal monohydrate), ASBA (4-(p-azidosalicylamido)-butylamine), BASED (bis(β-[4-azidosalicylamido]ethyl) disulfide), BMB (1,4-bis-maleimidobutane), BMDB (1,4-bis-maleimidyl-2,3-dihydroxybutane), BMH (bis-maleimidohexane), ZMOE (bis-maleimido ethane), BMPA (N-β-maleimidopropionic acid), BMPH (N-(β-maleimido propionic acid) hydrazide.TFA), BMPS (N-(β-maleimidopropyloxy)succinimide ester), BM [PEO]2 (1,8-Bis-maleimidodiethylene-glycol), BM [PEO] 3 (1,11-bis-maleimidotriethylene glycol), BS2G-d0 (bis(sulfosuccinimidyl) glutarate), BS2G-d4 (bis sulfosuccinimidyl) 2,2,4,4-glutarate), BS3 (Sulfo-DSS) (bis(sulfosuccinimidyl) suberate), BS3-d0 (bis (sulfosuccinimidyl)suberate), BS3-d4 (bis(sulfosuccinimidyl)2,2,7,7-suberate-d4), BS[PEG]5 (bis (NHS)PEO5), BSOCOES (bis(2-[succinimidoxycarbonyloxy]ethyl)sulfone), C6-SANH (C6-succinimidyl 4-hydrazinonicotinate acetone hydrazone), C6-SFB (C6-succinimidyl 4-formylbenzoate), DCC (N,N-dicyclohexylcarbodiimide), DFDNB (1-5-difluoro-2,4-dinitrobenzene), DMA (dimethyl adipimidate.2HCl), DMP (dimethyl pimelimidate.2HCl), DMS (dimethyl suberimidate.2HCl), DPDPB (1,4-di-(3'-[2'pyridyldithio]propionamido) butane), DSG (disuccinimidyl glutarate), DSP dithiobis(succimidylpropionate) (Lomant's Reagent)), DSS (disuccinimidyl suberate), DST (disuccinimidyl tartarate), DTBP (dimethyl 3,3'-dithiobispropionimidate.2HCl), DTME (dithiobis-maleimidoethane), DTSSP (Sulfo-DSP) (3,3'-Dithiobis (sulfosuccinimidyl propionate)), EDC (1-ethyl-3-(3-dimethylamino propyl), EGS (ethylene glycol bis(succinimidylsuccinate)), EMCA (N-ε-maleimidocaproic acid), EMCH (N-(ε-maleimidocaproic acid)hydrazide), EMCS (N-(ε-maleimidocaproyloxy) succinimide ester), GMBS N-(γ-maleimidobutyryloxy)succinimide ester), HBVS (1,6-hexane-bis-vinylsulfone), KMUA (N-κ-maleimido undecanoic acid), KMUH (N-(κ-maleimido undecanoic acid)hydrazide), LC-SMCC (succinimidyl 4-(N-maleimidomethyl)cyclohexane-1-carboxy-(6-amidocaproate)), LC-SPDP (succinimidyl 6-(3'-[2-pyridyl-dithio]propionamido) hexanoate), MBS (m-maleimidobenzoyl-N-hydroxysuccinimide ester), MPBH (4-(4-N-maleimidophenyl)-butyric acid hydrazide-.HCl), Mts-Atf-Biotin (2-[N 2-(4-azido-2,3,5,6-tetrafluorobenzoyl)-N 6-(6-biotinamidocaproyl)-L-lysinyl]ethyl-methanethiosulfate), Mts-Atf-LC-Biotin (2-{N 2-[N6-(4-azido-2,3,5,6-tetrafluorobenzoyl)-N 6-(6-biotinamidocaproyl)-L-lysinyl]}ethylmethanethiosulfate), NHS-ASA (N-hydroxysuccinimidyl-4-azidosalicylic acid), PDPH (3-(2-pyridyldithio)propionylhydrazide), PMPI (N-(p-maleimidophenyl)isocyanate), SADP (N-succinimidyl (4'-azidophenyl)1, 3'-dithiopropionate), SANH (succinimidyl 4-hydrazinonicotinate acetone hydrazone), SANPAH (N-succinimidyl 6-(4'-azido-2'-nitrophenylamino)hexanoate), SBAP (succinimdyl 3-(bromoacetamido)propionate), SFB (succinimidyl 4-formylbenzoate), SHTH (succinimidyl 4-hydrazidoterephthalate hydrochloride), SIA (N-succinimidyl iodoacetate), SIAB (N-succinimidyl(4-iodoacetyl) aminobenzoate), SMCC (succinimidyl 4-(N-maleimido-methyl)cyclohexane-1-carboxylate), SM[PEG]2 (NHS-PEO2-Maleimide), SM[PEG]4 (NHS-PEO4-Maleimide), SM[PEG]8 (NHS-PEO8-Maleimide), SM[PEG] 12 (NHS-PEO12-Maleimide), SMPB (succinimidyl 4-(p-maleimido-phenyl)butyrate), SMPH (succinimidyl-6-(β-maleimidopropionamido)hexanoate), SMPT (4-succinimidyloxy-carbonyl-methyl-α-(2-pyridyldithio)toluene), SPB (succinimidyl-(4-psoralen-8-yloxy)butyrate), SPDP (N-succinimidyl 3-(2-pyridyldithio)propionate), Sulfo-EGS (ethylene glycol bis(sulfo-succinimidyl succinate)), Sulfo-EMCS (N-(ε-maleimido caproyloxy)sulfosuccinimide ester), Sulfo-GMBS (N-(γ-maleimidobutryloxy) sulfosuccinimide ester), Sulfo-HSAB (N-hydroxy sulfosuccinimidyl-4-azidobenzoate), Sulfo-KMUS (N-(κ-maleimido undecanoyloxy) sulfosuccinimide ester), Sulfo-LC-SMPT (sulfo succinimidyl 6-(α-methyl-α-[2-pyridyldithio]-toluamido)hexanoate), Sulfo-LC-SPDP (sulfosuccinimidyl 6-(3'-[2-pyridyl-dithio]propionamido)hexanoate), Sulfo-MBS (m-Maleimidobenzoyl-N-hydroxysulfo succinimide ester), Sulfo-NHS-LC-ASA (sulfosuccinimidyl(4-azido-salicylamido) hexanoate), Sulfo-SADP (sulfosuccinimidyl(4-azido-phenyldithio)propionate), Sulfo-SAED (sulfosuccimidyl 2-[7-azido-4-methylcoumarin-3-acetamido]ethyl-1,3'-dithiopropionate), Sulfo-SAND (sulfosuccinimidyl-2-(m-azido-o-nitrobenzamido) ethyl 1,3'-dithiopropionate), Sulfo-SANPAH (sulfosuccinimidyl 6-(4'-azido-2'-nitrophenylamino)hexanoate), Sulfo-SASD (sulfosuccinimidyl 2-(p-azido-salicylamido) ethyl 1,3'-dithiopropionate), Sulfo-SBED (sulfo-NHS-(2-6-[biotinamido]-2-(p-azido benzamido) hexanoamido)ethyl-1, 3'-dithiopropionate (trifunctional), Sulfo-SFAD (sulfosuccinimidyl(perfluoroazidobenzamido) ethyl 1,3'-dithiopropionate), Sulfo-SIAB (sulfosuccinimidyl(4-iodoacetyl)aminobenzoate, Sulfo-SMCC (sulfosuccinimidyl 4-(N-maleimidomethyl)cyclohexane-1-carboxylate), Sulfo-SMPB (sulfosuccinimidyl 4-(p-maleimidophenyl)butyrate), THPP γ-(tris[hydroxymethyl]phosphine)propionic acid) (betaine), TMEA tris-(2-maleimido ethyl)amine (trifunctional), TSAT (tris-(succimimidyl aminotricetate)) (trifunctional), and preferably hexane-1,6-dicarboxylic acid (suberic acid).

For forming a desired three-dimensional form of the scaffolding matrix, the spider silk segments and a cross-linking agent are introduced into a pressing form, e.g. between two mould halves having approximately the shape and dimension required for implantation, e.g. the form required for filling a tissue defect.

For providing an implant comprising cells adhering to the matrix, in general cells of the cell type are preferred which is predominantly and naturally occurring in the natural healthy tissue to be replaced.

According to the second embodiment, the spider silk threads are used for the production of a simple arrangement of spider silk threads to cover the surface of the wound to be treated, e.g. in the form of a woven, preferably non-woven tissue, for example as an arrangement of parallel or crossing sections or segments of spider silk threads. In a simple manner, such a non-woven tissue can be produced by winding the major ampullate on a rotating drum or around any two or more spaced elements and cutting the coiled thread in parallel to the winding axis. As a result, an arrangement of loosely associated, essentially parallel spider silk sections is obtained.

Optionally, the arrangement of spider thread segments or sections to a woven or non-woven tissue can be cross-linked by a cross-linking agent according to the first embodiment to stabilise its shape. However, it is preferred that the cross-linking is such that the non-woven tissue of spider thread segments or sections is compliant and elastic to comply to the shape of a wound surface.

As a specific advantage of the second embodiment, it has been observed that wound surfaces are efficiently covered the tissue of the invention simply by the spider thread tissue adhering to the moist wound surfaces without the need for more attachment than provided by simple surface contact.

The following examples describe use of the tissue and cross-linked matrix of the invention for the production of specific medical products that can be used as implants for filling or replacing a tissue defect in a mammal, e.g. in humans.

EXAMPLE 1

Use of Spider Silk for the Production of a Wound Dressing for Treating Wetting and/or Non-Healing Wounds For the treatment of a non-healing wound, exemplified by a venous ulcer in a sixty-five year-old female patient, a tissue made up of an arrangement of spider silk threads was used. The patient has a long history of venous ulcer, which using state of the art treatment could not be healed to regenerate a closed surface, preferably a normal skin surface. Instead, the patient regularly returned once or twice a year to the hospital for renewed treatment of the venous ulcer that was a constantly wetting superficial wound.

With consent of the patient, the wound was covered with a non-woven tissue of spider dragline silk threads, that were obtained from *Nephila clavipes* under sterile conditions. Except for cutting a coil of dragline silk in parallel to the axis of winding, no further treatment was required to obtain the non-woven tissue wound dressing. The mean fibre density was approximately between 10 to 5000, preferably 100 to 1000 threads/cm$^2$. Dimensions were chosen between approximately 0.5 and 15 cm each side at a theoretical thickness of a few thread diameters. The arrangement of fibres perpendicular to the desired generally flat shape was not problematic because essentially all fibres quickly adhere to the moist wound surface.

After application of the spider silk wound dressing, the wound was optionally loosely covered to hinder secondary infections. However, the coverage in addition to the tissue according to the invention was no prerequisite for healing of the wound.

Without additional medication, the venous ulcer after just one treatment with the spider silk tissue of the invention was healing to a closed skin surface after 10 to 20 days.

As a further example of superficial lesions with a seroserous or serosanguineous characteristic, decubitus ulcers in male and female patients having an age of 50 to 85 years were successfully treated by application of the spider silk tissue according to the invention. As described above, the wound surface was covered with a non-woven tissue of dragline spider silk.

In the alternative to using a loose arrangement in the form of a non-woven tissue obtained by cutting a coil of dragline threads in parallel to the winding axis, the non-woven tissue was cross-linked, e.g. by incubation with an aqueous solution of suberic acid for 45 min at room-temperature, followed by extensive washing in PBS under sterile conditions. The concentration of the cross-linking agent was adjusted such that the minimal concentration for obtaining a linkage between fibres was generated in order to avoid further chemical modification of the fibres' surface. The desired flat shape of the non-woven tissue was obtained by gently pressing the arrangement of fibre segments between two planar surfaces or between mating concave and convex surfaces, respectively. The cross-linked tissue has the advantage of allowing a more simple manipulation than without cross-linking, e.g. when covering the wound surface.

From these experimental treatments, the overwhelming efficacy of the tissue essentially consisting of spider silk threads in respect of wound healing for wounds that have a seroserous or serosanguineous characteristic are demonstrated, wherein the wounds may even include possible superficial infections. Similar results were obtained for cross-linked and non-cross-linked non-woven tissues of dragline spider threads.

These results could even be obtained in wounds that a known history of being essentially untreatable by conventional medical treatment. In some of the cases cited here, conventional treatment prior to the application of the silk tissue included the application of antiseptic agents, including antibiotics, and the application of vacuum assisted closure therapy (V.A.C., KCI) to promote wound healing. However, the conventional treatments did not or only very slowly result in the generation of skin at the affected areas.

EXAMPLE 2

Three-Dimensional Implant Consisting of Cross-Linked Spider Silk Threads

In this example, the suitability of the three-dimensional implant consisting of cross-linked spider thread sections is demonstrated. The three-dimensional implant was shaped by moulding to conform to the tissue defect to be replaced by the implant, e.g. a full or partial columella replacement.

The moulds for forming the desired scaffolding matrix was custom made according to the required dimensions of the columella to be replaced, using computer tomographs, X-rays and ultrasound measurements. The two half moulds were shaped from sterilizable synthetic polymer, e.g. polyamide such that the mould cavity essentially corresponded to the desired three-dimensional form of the implant.

Spider silk was obtained from *Nephila clavipes* by winding of the major ampullate thread at a speed of approximately 5 m/s onto a rotating drum having a diameter of 5 cm from a mechanically fixed female spider in a sterile environment. The spider silk could be used for moulding and cross-linking without further size reduction, e.g. only cut once or twice in parallel to the winding axis of the coil for simple removal of the threads from the winding apparatus. Preferably, the coil of spider silk was fragmented by homogenization in a sterile PBS solution (phosphate buffered saline) using a shaving foil homogenizer or an ultrasound homogenizer. The average length of fibre fragments was from 0.2 or 1 to 10 mm.

The fibre fragment suspension was collected by centrifugation at 13,000 rpm and resuspended to a concentration of about 10 mg/mL in PBS. The suspension was filled into the mould. The cross-linking agent, in the present case hexane 1,6-dicarboxylic acid was added to a final concentration in the range of 1 to 5 mM, preferably 4.4 mM, e.g. 2.53 mg/mL. Closing the mould for 15 to 30 minutes at room temperature, the silk thread sections and/or fragments are formed into a dense matrix having a pore size of about 10 to 1000 preferably of about 50 to 150

For allowing the aqueous medium of the suspension to exit the mould, the mould was equipped with exit openings of 0.5 to 2 mm diameter.

Following the moulding process, the mould halves were separated again and the three-dimensional scaffolding matrix could be retrieved from the half moulds.

For stopping the cross-linking reaction, the three-dimensional matrix could be incubated in 0.2 M Tris-HCl, pH 7.5 at room temperature and then washed with PBS.

The implant was used for implantation into a laboratory animal, replacing a portion of the columella. Following 10 to 20 days, colonization of the implant with local cells was observed. The columella implant was fully functional after 15-17 days following implantation.

EXAMPLE 3

Implant Comprising a Three-Dimensional Scaffolding Matrix Colonized with Autologous Cells In a further embodiment of the implant according to Example 2, the three-dimensional scaffolding matrix was colonized with autologous cells derived from the later recipient of the implant by incubation in conventional cell culture medium containing foetal calf serum (FCS) or serum free medium.

The scaffolding matrix comprised of cross-linked spider silk sections was incubated in a bio-reactor, in which the medium was gassed bubble-free and agitated, optionally by circulation and/or partial exchange of the medium with an outside reservoir. The medium was conventional cell culture medium with 5% FCS.

Autologous cells could be obtained by biopsies, purified from neighbouring undesired tissue and propagated in cell culture. For covering the three-dimensional scaffolding matrix with the desired cell types, cells were added to the bio-reactor, wherein the matrix was suspended. Initially, a cell density of about 1,000,000 cells/cm$^2$ of assumed closed outer surface of the matrix geometry was found to yield satisfactory results.

Cells that were isolated for colonizing the matrix were selected depending on the nature of the desired implant, generally using cell types corresponding to the cell type found in the natural tissue to be replaced by the implant. For example, for producing a columella implant, cells purified from a biopsy of the anvil or hammer were used.

Currently, it is believed that the observation of different cell types used quickly adhering to the matrix, therefore leading to a depletion of suspended free cells from the circulating or surrounding medium, is caused by the nature of the spider silk threads obtained in their natural structure and composition.

Following the adhesion of suspended cells from the culture medium to the matrix, the incubation is continued until a desired cell density of the implant was achieved, generally at a cultivation time of 1 to 20 days at 37° C. in a 5% $CO_2$ atmosphere. The solidity and structural integrity of the implant was attributed to the cross-linked moulded matrix.

Following the colonization of the matrix with cells, the implant was retrieved from the bio-reactor and used for implantation directly, avoiding an extended contact of the implant with the surrounding atmosphere.

Figure 1:
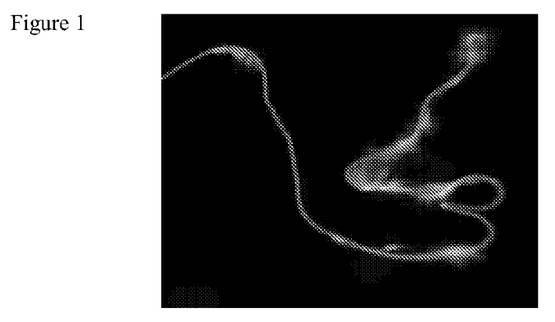
FIGS. 1 to 3 show micrographs of a scaffolding matrix of the invention comprising adhering cells.
Figure 2:
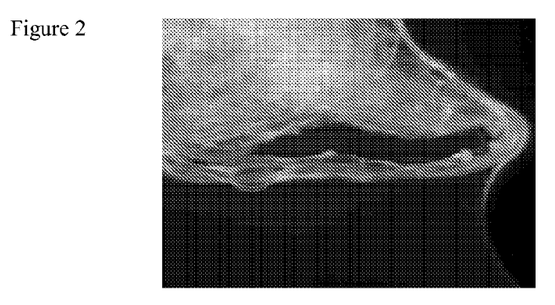
Figure 3:
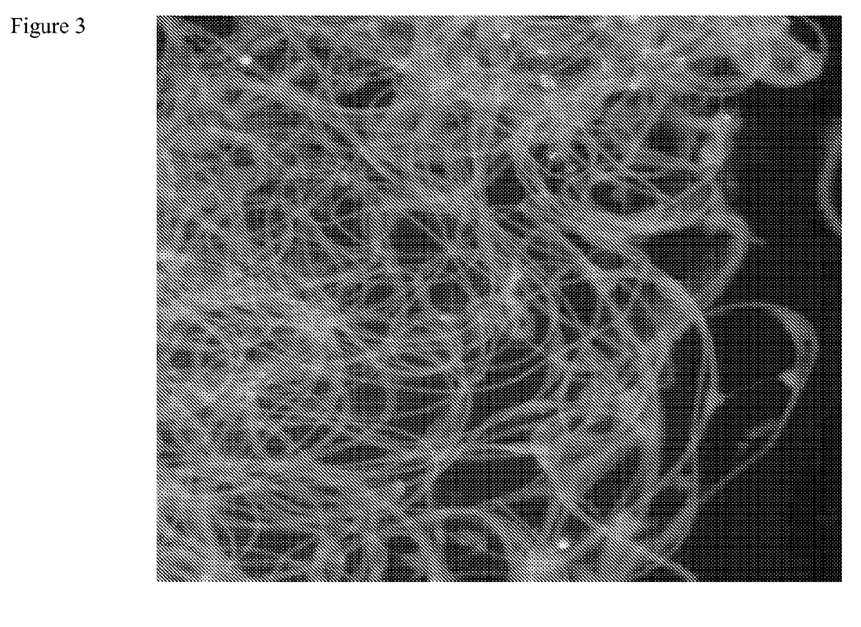

The result of an in vitro colonization of a scaffolding matrix generated according to example 2 is shown in FIGS. 1 to 3. The microscopic views having an original enlargement of 100× show the threads of the matrix and adhering mouse fibroblast cells (NIH 3T3) after 2 hours of incubation in cell culture medium. Dying of cells demonstrates that the vast majority of cells adhere to the scaffolding matrix and are vital, whereas only very few cells can be detected as dead (bright spots in FIG. 3 are nuclei of dead cells).

Further implants that could be produced are heart valve implants comprising the scaffolding matrix of the invention, which matrix was colonized with autologous adult mesenchymal stem cells or progenitor cells, e.g. derived from bone marrow, using in vitro cultivation of the cells with the matrix. For heart valves, the scaffolding matrix was shaped by moulding to correspond to the natural shape and dimensions of the heart valves to be replaced. For colonizing of the scaffolding matrix, cells obtained from a biopsy were used.

When implanting such a heart valve into an experimental animal (pig), attachment of the implant by standard surgical procedures yielded a functional implant. Adverse immunological reactions were not observed. Further, no deposits on the implant could be found.

EXAMPLE 4

Dermis Implant

For producing a dermis implant for medical use, it is preferred to provide a cross-linked non-woven tissue of spider silk segments, and preferably colonized with cells, preferably autologous cells of the implant recipient. The implant is obtainable by cultivation of the scaffolding matrix with the cells.

For production of a dermis implant, the scaffolding matrix is essentially flat, for example produced by colonizing a cross-linked sheet of cut or uncut spider thread, cross-linked in a mould having inner dimensions of a height of 0.5 to 3 mm, preferably 1 to 2 mm with a surface in the desired dimensions, e.g. having edges of 1 to 9 cm, respectively.

For growth of the naturally occurring cell types within the scaffolding matrix, the scaffolding matrix is incubated in a bio-reactor with keratinocytes and fibroblasts. Preferably, the scaffolding matrix is first incubated under cultivation conditions with fibroblasts until the fibroblasts achieve a confluent cell layer on the matrix. In a second step, keratinocytes are added to the scaffolding matrix and, following an additional cultivation time of 3 to 5 days, the colonized matrix is incubated in a bio-reactor allowing the exposure of one surface to sterile air including 5% $CO_2$.

In order to expose one side of the sheet-like implant to a gaseous atmosphere, the scaffolding matrix can be removed from submerged cultivation to a flat culture dish, allowing the exposure of one side of the sheet-like implant to a gaseous atmosphere, while the opposite side is contacted with cell culture medium. Using experimental animals, it could be shown that artificial implants for the replacement of dermis can be generated, which implants can be integrated into skin lesions for coverage of underlying tissue.

EXAMPLE 5

Artificial Vessel Implant

In accordance with example 2, a tube-like implant was generated by moulding skin silk segments into a tube-like shape in the presence of hexane 1,6 dicarboxylic acid.

The resulting scaffolding matrix in the form of a tube was incubated in a tube-like reactor, preferably having inner dimensions corresponding to the outer dimensions of the scaffolding matrix, with the major volume of the cell culture medium present in the inner volume of the matrix. Using autologous endothelial cells from the future implant recipient, the colonization of the matrix with endothelial cells could be achieved by cultivation. Because nutrient and oxygen concentrations were optimal at the inner surface of the matrix, predominant colonization of the inner surface was achieved.

In the alternative, the cylindrical bio-reactor was arranged to rotate along its horizontally oriented longitudinal axis in combination with only partial filling of the inner volume of the matrix with culture medium. As a result of the horizontal rotation of the tube-like matrix predominant colonization of the inner surface of the matrix with endothelial cells was generated.

In a subsequent step, autologous fibroblasts and/or muscle cells could be added to the cell culture medium, resulting in a predominant localization of the fibroblasts and/or muscle cells within the matrix and on the outer surface of the tube-like matrix, respectively. For this secondary addition of another cell type, a bioreactor can be used in which the matrix is suspended and completely covered by cell culture medium.

As a result, functional vessel implants having a sufficient stability for implantation could be generated. Following a period of 2 to five months after implantation, experimental animals showed that the implants generally had a structure corresponding to natural vessels, including the typical distribution of cell types.

This example demonstrates that functional implants can be generated that also have the advantage of any foreign material originally contained in the implant being completely dissolved and replaced by autologous cells and tissue. As a consequence, the implant can follow the growth of the implant recipient without the need for adaptation of the size of the implant by later replacements of the implant.

Similar to the generation of the vessel implant, a urethral implant could be generated using a tube-like scaffolding matrix. For the urethral implant, it is preferred to first colonize the scaffolding matrix on its inner surface with urothelial cells, preferably obtained from the future implant recipient. While the implant has sufficient stability for implantation while colonized at least on its inner surface with urothelial cells, it is preferred to have the outer surface of the tube-like scaffolding matrix colonized with autologous muscle cells.

Following the implantation, inner longitudinal muscle tissue as well as outer circular muscle tissue generated within the implant recipient. The generation of inner and outer muscle tissue is accelerated by previous incubation of the scaffolding matrix with muscle cells. Implantation into experimental animals demonstrates that the implant comprising urothelial cells at least on its inner surface are functional implants to replace the defective or missing tissue.

EXAMPLE 6

Cartilage Implant

Cartilage implants are generated according to the present invention by colonizing the three-dimensional scaffolding matrix of cross-linked spider silk with chondrocytes. Preferably, autologous chondrocytes obtained from the future recipient of the implant are used. The cultivation of chondrocytes with the three-dimensional scaffolding matrix leads to the colonization of the matrix by the chondrocytes, which can be cultivated in vitro to form a stable cartilage tissue. In this product, the natural collagen fibres are formed instead by spider silk threads. However, after implantation of the implant into a recipient mammal, the spider silk and threads are dissolved and the generation of collagen fibres can be observed.

EXAMPLE 7

Bone Implant

Bone implants generated according to the present invention can still be considered soft tissue implants because the final density and stability of natural bone tissue can usually not be produced artificially without additionally applying mechanical stress during in vitro cultivation. However, after implantation of a bone implant according to the invention, the site of the implant acquires the properties of the bone tissue of the recipient, including its natural density and stability.

In detail, a scaffolding matrix is moulded to acquire the shape necessary for filling the bone defect in the future recipient, the matrix being formed of cross-linked spider silk segments. Preferably using autologous osteoblasts, optionally in mixture with osteocytes, the matrix is incubated in cell culture medium for colonization with bone tissue. Following a cultivation over a period of 5 to 20 days, including regular complete or partial changes of conventional cell culture medium, the implant maintains the three-dimensional shape of the originally moulded matrix and is colonized densely with bone tissue.

After implantation of the implant, the bone defect is filled by the implant, which after some time acquires the properties of the natural bone tissue to an extent of forming a functional implant.

EXAMPLE 7

Bowman's Membrane and Cornea Implant

As a further embodiment of the invention, a cornea implant was generated by progressive colonization of a scaffolding matrix consisting of cross-linked spider silk threads, each with one the main cell types of the cornea adhering, e.g. epithelial, stromal, and endothelial cells, respectively.

In detail, a sheet-like matrix of cross-linked spider silk segments was seeded with endothelial cells for 24 hours under standard cell culture conditions using e.g. in DMEM supplemented with 10% FCS in a humidified 37° C., 5% $CO_2$ atmosphere. Then, a stroma substitute was made by cultivating keratocytes with another layer of cross-linked spider silk matrix for another 24 hours under standard cell culture conditions to obtain cells entrapped in or adhering to the scaffolding matrix. Finally, cultured corneal epithelial cells were grown on the surface of the scaffold for at least two weeks under standard cell culture conditions. Stratification of the epithelial cell layer was promoted by using an air-liquid culture technique after the epithelial cell layer reached confluence.

The implants could replace the natural tissue or used in cornea models for pharmacological purposes.

EXAMPLE 8

Ligament and Tendon Implants

Further ligament and tendon implants according to the invention were generated by colonizing a three-dimensional scaffolding matrix, which was e.g. moulded into a longitudinal shape having a round or elliptic cross-section by cultivation in an agitated bio-reactor with bone marrow stroma cells and/or fibroblasts.

Following cultivation until a confluent colonization of the scaffolding matrix was achieved, the implant could be transferred to an implant recipient, exemplified by a laboratory animal. Fixation of the respective ends of the implant to the bone was done by screws located in holes drilled into the bone for fixation.

The dimensions of the implant were chosen such that bending of the joint was possible while stretching the implant to a maximum of 20 to 5% in length. After a period of four weeks to four months following the implantation, the ligament or tendon implant was further colonized by cells originating from the implant recipient, generally forming a structure of the implant similar to the natural structure of ligaments and tendons in the recipient while the original matrix disappeared.

EXAMPLE 9

Dura Mater Implant

As a further application of the implant according to the invention, a dura mater implant, e.g. dura mater of brain or dura mater of spinal cord could be generated by in vitro colonization of a scaffolding matrix with autologous cells.

In detail, a sheet-like matrix of cross-linked spider silk segments was incubated with adult mesenchymal stem cells and endothelial progenitor cells, e.g. derived from the bone marrow obtained from the future recipient in cell culture medium for the period of 7 to fourteen days. After colonization of the scaffolding matrix with the adult mesenchymal stem cells or progenitor cells, e.g. derived from the bone marrow, the implant could be implanted into a laboratory animal, replacing a portion of the dura mater of brain and/or dura mater of spinal cord. The implants could be shown to replace the function of the natural tissue, at least following a period of six weeks to six months following implantation.

EXAMPLE 10

Ureter Implant

In accordance with example 5, a tube-like implant was generated by moulding skin silk segments into a tube-like shape in the presence of hexane 1,6 dicarboxylic acid. The resulting scaffolding matrix was seeded with autologous genitourinary-associated cells, e.g. urothelial cells.

Cultivation of the cells in the three-dimensional matrix lead to the growth of a complete epithelial layer on the inside surface of the tube. After completion of a closed epithelial layer, the implant was implanted into a recipient mammal. Following implantation, it was observed that the epithelial cell layer is strengthened by additional cell layers and that the cross-linked spider silk matrix is slowly degraded in the recipient animal and replaced with host tissue.

The invention claimed is:

1. Method for the production of implants for medical use, comprising: mixing spider silk thread segments and a cross-linking agent in the absence of any bulk matrix compound to provide a scaffolding matrix, and molding the scaffolding matrix of cross-linked spider silk threads into a pre-determined three-dimensional form, with no addition of a bulk matrix compound.

2. Method according to claim 1, wherein the scaffolding matrix comprises adherent mammalian cells by in vitro cultivation.

3. Method according to claim 2, wherein the cells are obtained from the future recipient of the implant or are immunologically tolerated heterologous cells.

4. Method according to claim 2 wherein the mammalian cells are obtained from the future recipient and the cultivation comprises incubating the scaffolding matrix with the cells under cell culture conditions.

5. Method according to claim 1, wherein the spider silk thread segments have a length in the range of 0.1 mm to 200 mm.

6. Method according to claim 1, wherein said molding comprises using a die cavity formed between two half moulds.

7. Method according to claim 1 for the replacement of a tissue defect.

8. Implant for medical use comprising spider silk threads, characterized in that the implant is a scaffolding matrix having a predetermined three-dimensional form, obtainable by moulding spider silk threads obtainable from spiders in the presence of a cross-linking agent, with no addition of a bulk matrix compound.

9. The implant of claim 8, applied to a seroserous or serosanguineous wound.

10. The implant of claim 8, wherein the spider silk threads are formed into a non-woven tissue.

11. Implant according to claim 8, wherein the implant comprises adherent cells.

12. Implant according to claim 11, wherein the cells are obtained from the future recipient of the implant.

13. Implant according to claim 8, wherein the spider silk threads have a length in the range of 0.1 mm to 200 mm.

14. Implant for medical use consisting of a scaffolding matrix consisting of cross-linked spider silk threads moulded into a pre-determined three-dimensional form with only a cross-linking agent.

* * * * *

UNITED STATES PATENT AND TRADEMARK OFFICE
CERTIFICATE OF CORRECTION

PATENT NO. : 8,696,762 B2  Page 1 of 1
APPLICATION NO. : 12/518638
DATED : April 15, 2014
INVENTOR(S) : Peter Vogt It is certified that error appears in the above-identified patent and that said Letters Patent is hereby corrected as shown below:

On the Title Page:

(57) ABSTRACT

Line 8

Between "molding" and "sufficiently", please insert --is--.

In the Specification:

Col. 6, line 42    After "covered", please insert --by--.

Signed and Sealed this
Eighteenth Day of November, 2014

Michelle K. Lee
*Deputy Director of the United States Patent and Trademark Office*